(12) United States Patent
Saito (10) Patent No.: US 10,709,408 B2
(45) Date of Patent: Jul. 14, 2020

(54) MEDICAL IMAGE DIAGNOSIS APPARATUS AND CONTROL METHOD

(71) Applicant: Toshiba Medical Systems Corporation, Otawara-shi (JP)

(72) Inventor: Yasuo Saito, Nasushiobara (JP)

(73) Assignee: CANON MEDICAL SYSTEMS CORPORATION, Otawara-shi (JP)

(*) Notice: Subject to any disclaimer, the term of this patent is extended or adjusted under 35 U.S.C. 154(b) by 737 days.

(21) Appl. No.: 14/953,203

(22) Filed: Nov. 27, 2015

(65) Prior Publication Data

US 2016/0073974 A1  Mar. 17, 2016

Related U.S. Application Data

(63) Continuation of application No. PCT/JP2014/064179, filed on May 28, 2014.

(30) Foreign Application Priority Data

May 28, 2013 (JP) .................. 2013-112332

(51) Int. Cl.
*A61B 6/03* (2006.01)
*A61B 6/00* (2006.01)
*A61B 6/06* (2006.01)

(52) U.S. Cl.
CPC .............. *A61B 6/545* (2013.01); *A61B 6/032* (2013.01); *A61B 6/035* (2013.01); *A61B 6/06* (2013.01);
(Continued)

(58) Field of Classification Search
CPC ......... A61B 6/032; A61B 6/06; A61B 6/4035; A61B 6/4233; A61B 6/469; A61B 6/5205;
(Continued)

(56) References Cited

U.S. PATENT DOCUMENTS 5,541,971 A * 7/1996 Saito ............... A61B 6/032 378/15
5,907,594 A * 5/1999 Lai ................. A61B 6/032 378/15

(Continued)

FOREIGN PATENT DOCUMENTS

JP 10-248835 9/1998
JP 11-19078 1/1999
(Continued)

OTHER PUBLICATIONS

International Search Report dated Aug. 26, 2014 in PCT/JP2014/064179 filed May 28, 2014 (with English Translation).
(Continued)

*Primary Examiner* — Allen C. Ho
(74) *Attorney, Agent, or Firm* — Oblon, McClelland, Maier & Neustadt, L.L.P.

(57) ABSTRACT

A medical image diagnosis apparatus according to an embodiment includes an input circuitry, a scan control circuitry, and a reconstruction control circuitry. The input circuitry receives a specifying operation for specifying, from a region of a first medical image acquired such that the first medical image contains less noise, a region for which a second medical image that is a higher-definition image than the first medical image is acquired. The scan control circuitry adjusts an irradiation region of X-rays in a slice direction and a channel direction such that a part corresponding to the region on which the specifying operation is received by the input circuitry is irradiated with the X-rays. The reconstruction control circuitry performs reconstruction, on the first medical image as an initial image, by the successive approximation method by using projection data collected after the irradiation region of the X-rays is adjusted by the scan control circuitry.

7 Claims, 7 Drawing Sheets

(52) U.S. Cl.
CPC ............. *A61B 6/4035* (2013.01); *A61B 6/42* (2013.01); *A61B 6/4208* (2013.01); *A61B 6/4233* (2013.01); *A61B 6/46* (2013.01); *A61B 6/461* (2013.01); *A61B 6/467* (2013.01); *A61B 6/52* (2013.01); *A61B 6/5258* (2013.01); *A61B 6/54* (2013.01); *A61B 6/542* (2013.01); *A61B 6/469* (2013.01); *A61B 6/5205* (2013.01); *A61B 6/56* (2013.01)

(58) Field of Classification Search
CPC .. A61B 6/54; A61B 6/542; A61B 6/42; A61B 6/4208; A61B 6/035; A61B 6/46; A61B 6/461; A61B 6/467; A61B 6/52; A61B 6/5258; A61B 6/545; A61B 6/56
USPC .................. 378/16, 19, 62, 150–152, 15
See application file for complete search history.

(56) References Cited

U.S. PATENT DOCUMENTS

| | | | | |
|---|---|---|---|---|
| 6,385,278 B1* | 5/2002 | Hsieh | A61B 6/032 378/15 |
| 6,445,761 B1 | 9/2002 | Miyazaki et al. | |
| 6,459,755 B1* | 10/2002 | Li | A61B 6/032 378/4 |
| 6,856,666 B2 | 2/2005 | Lonn | A61B 6/032 378/19 |
| 6,922,457 B2* | 7/2005 | Nagata | A61B 6/032 378/15 |
| 7,054,409 B2* | 5/2006 | Ross | A61B 6/032 250/370.09 |
| 7,076,019 B2* | 7/2006 | Hagiwara | A61B 6/032 378/16 |
| 7,085,343 B2* | 8/2006 | Shinno | A61B 6/032 378/19 |
| 7,103,134 B2* | 9/2006 | Suzuki | A61B 6/032 378/4 |
| 7,113,569 B2* | 9/2006 | Okumura | A61B 6/032 378/150 |
| 7,203,270 B2* | 4/2007 | Okumura | A61B 6/032 378/109 |
| 7,272,205 B2* | 9/2007 | Thibault | A61B 6/032 378/4 |
| 7,349,520 B2* | 3/2008 | Nakashima | A61B 6/032 378/4 |
| 7,359,535 B2* | 4/2008 | Salla | A61B 6/032 378/4 |
| 7,376,255 B2* | 5/2008 | De Man | G06T 11/005 378/4 |
| 7,394,923 B2* | 7/2008 | Zou | G01N 23/046 378/4 |
| 7,466,790 B2* | 12/2008 | Suryanarayanan | A61B 6/032 378/4 |
| 7,492,934 B2* | 2/2009 | Mundy | A61B 6/5217 382/128 |
| 7,680,240 B2* | 3/2010 | Manjeshwar | A61B 6/032 378/4 |
| 7,693,252 B2* | 4/2010 | Noshi | A61B 6/00 378/4 |
| 7,729,467 B2* | 6/2010 | Kohlmyer | A61B 6/032 250/363.04 |
| 7,756,240 B2* | 7/2010 | Nishide | A61B 6/4035 378/5 |
| 7,764,763 B2* | 7/2010 | Mori | A61B 6/032 378/11 |
| 7,885,374 B2* | 2/2011 | Noshi | A61B 6/032 378/15 |
| 7,920,670 B2* | 4/2011 | Hugg | A61B 6/032 378/4 |
| 7,978,810 B2* | 7/2011 | Schwarz | A61B 6/027 378/19 |
| 8,031,828 B1* | 10/2011 | DeMan | G06T 11/005 378/15 |
| 8,135,186 B2* | 3/2012 | Bouman | G06T 11/006 378/19 |
| 8,139,709 B2* | 3/2012 | Noo | G06T 11/006 378/19 |
| 8,184,768 B2* | 5/2012 | Honda | A61B 6/032 378/134 |
| 8,306,304 B2* | 11/2012 | Noo | A61B 6/032 378/15 |
| 8,410,448 B2* | 4/2013 | Forthmann | A61B 6/032 250/370.09 |
| 8,548,118 B2* | 10/2013 | Hsieh | A61B 6/482 378/124 |
| 8,553,959 B2* | 10/2013 | Hsieh | A61B 6/032 382/131 |
| 8,558,176 B2* | 10/2013 | Komori | A61B 6/032 250/336.1 |
| 8,649,480 B2* | 2/2014 | Yoshida | A61B 6/032 378/16 |
| 8,731,267 B2* | 5/2014 | Nakanishi | G06T 11/005 382/131 |
| 8,755,585 B2* | 6/2014 | Nakanishi | A61B 6/032 382/131 |
| 8,792,610 B2* | 7/2014 | Miyazaki | A61B 6/4021 378/12 |
| 8,971,607 B2* | 3/2015 | Goto | G06T 11/003 382/131 |
| 9,050,003 B2* | 6/2015 | Takahashi | A61B 6/032 |
| 9,095,259 B2* | 8/2015 | Roshi | A61B 6/032 |
| 9,161,732 B2* | 10/2015 | Takayama | A61B 6/032 |
| 9,237,874 B2* | 1/2016 | DeMan | A61B 6/032 |
| 9,239,301 B2* | 1/2016 | Kikuchi | G06T 11/006 |
| 9,336,612 B2* | 5/2016 | Brown | G06T 5/50 |
| 9,406,121 B2* | 8/2016 | Goto | G06T 5/001 |
| 9,408,578 B2* | 8/2016 | Schmidt | A61B 6/032 |
| 9,462,988 B2* | 10/2016 | Hansis | G06T 11/005 |
| 9,466,131 B2* | 10/2016 | Ohishi | A61B 6/5235 |
| 9,495,772 B2* | 11/2016 | Shen | G01T 1/2985 |
| 9,538,972 B2* | 1/2017 | Mukumoto | A61B 6/463 |
| 9,592,021 B2* | 3/2017 | Yamakawa | A61B 6/032 |
| 9,592,023 B2* | 3/2017 | Tanaka | A61B 6/032 |
| 9,597,041 B2* | 3/2017 | Claus | A61B 6/032 |
| 9,672,640 B2* | 6/2017 | Kleiner | A61B 6/032 |
| 9,696,452 B2* | 7/2017 | Schafer | A61B 6/032 |
| 9,826,952 B2* | 11/2017 | Nakazawa | A61B 6/032 |
| 9,924,916 B2* | 3/2018 | Kato | A61B 6/482 |
| 10,130,320 B2* | 11/2018 | Saito | A61B 6/032 |
| 10,247,682 B2* | 4/2019 | Schlecht | A61B 6/032 |
| 2003/0076920 A1 | 4/2003 | Shinno et al. | |
| 2006/0274877 A1 | 12/2006 | Noshi et al. | |
| 2011/0280459 A1 | 11/2011 | Nakanishi et al. | |
| 2011/0299655 A1 | 12/2011 | Takayama | |
| 2013/0028500 A1 | 1/2013 | Takahashi et al. | |
| 2013/0223719 A1 | 8/2013 | Ohishi et al. | |

FOREIGN PATENT DOCUMENTS

| | | |
|---|---|---|
| JP | 11-28202 | 2/1999 |
| JP | 11-332862 | 12/1999 |
| JP | 2000-157534 | 6/2000 |
| JP | 2001-104292 | 4/2001 |
| JP | 2003-116833 | 4/2003 |
| JP | 2003-153893 | 5/2003 |
| JP | 2004-180715 | 7/2004 |
| JP | 2006-14822 | 1/2006 |
| JP | 2007-14755 | 1/2007 |
| JP | 2011-239888 | 12/2011 |
| JP | 2012-13680 | 1/2012 |
| JP | 2012-96023 | 5/2012 |
| WO | WO 2011/122613 A1 | 10/2011 |

OTHER PUBLICATIONS

Written Opinion dated Aug. 26, 2014 in PCT/JP2014/064179 filed May 28, 2014.

(56) References Cited

OTHER PUBLICATIONS

Office Action dated Dec. 11, 2018 in Japanese Patent Application No. 2014-110585.

* cited by examiner

MEDICAL IMAGE DIAGNOSIS APPARATUS AND CONTROL METHOD

CROSS-REFERENCE TO RELATED APPLICATIONS

This application is a continuation of PCT international application Ser. No. PCT/JP2014/064179 filed on May 28, 2014 which designates the United States, incorporated herein by reference, and which claims the benefit of priority from Japanese Patent Applications No. 2013-112332, filed on May 28, 2013, incorporated herein by reference. The entire contents of the prior Japanese Patent Application No. 2014-110585, filed on May 28, 2014, are also incorporated herein by reference.

FIELD

Embodiments described herein relate generally to a medical image diagnosis apparatus and a control method.

BACKGROUND

Conventional X-ray computed tomography (CT) apparatus emit X-rays to a subject and detect the X-rays that have passed through the subject to collect projection data, and reconstruct images from the collected projection data. The spatial resolution of a typical X-ray CT apparatus is about 0.35 mm. The spatial resolution of such an X-ray CT apparatus is determined by, for example, pixel size and pixel pitch of a detector and the X-ray focal spot size.

Recent X-ray CT apparatus have been focusing on increasing the maximum resolution. According to a report, some X-ray CT apparatus have achieved the spatial resolution of about 0.12 mm by reducing the pixel size of the detector and/or the X-ray focal spot size, for example. The X-ray CT apparatus usually use the convolution back projection method to reconstruct images, but some X-ray CT apparatus these days use the successive approximation method in reconstructing the images to reduce noise.

In the conventional technology described above, however, the X-ray CT apparatus have, in some cases, difficulty in both preventing an increase in radiation dose and acquiring a high-resolution image of a region that an observer wants to observe.

DETAILED DESCRIPTION

According to an embodiment, a medical image diagnosis apparatus includes an input circuitry and processing circuitry. The input circuitry is configured to receive a specifying operation for specifying, from a region of a first medical image acquired such that the first medical image contains less noise, a region for which a second medical image that is a higher-definition image than the first medical image is acquired. The processing circuitry is configured to adjust an irradiation region of X-rays in a slice direction and in a channel direction so that a part corresponding to the region on which the specifying operation is received by the input circuitry is irradiated with the X-rays. The processing circuitry is configured to perform reconstruction, on the first medical image as an initial image, by a successive approximation method by using projection data collected after the irradiation region of the X-rays is adjusted.

The following describes embodiments of a medical image diagnosis apparatus and a control method according to the present disclosure in detail with reference to the accompanying drawings. Hereinafter, the medical image diagnosis apparatus according to the embodiments is described in the context of an X-ray CT apparatus.

First Embodiment

Figure 1:
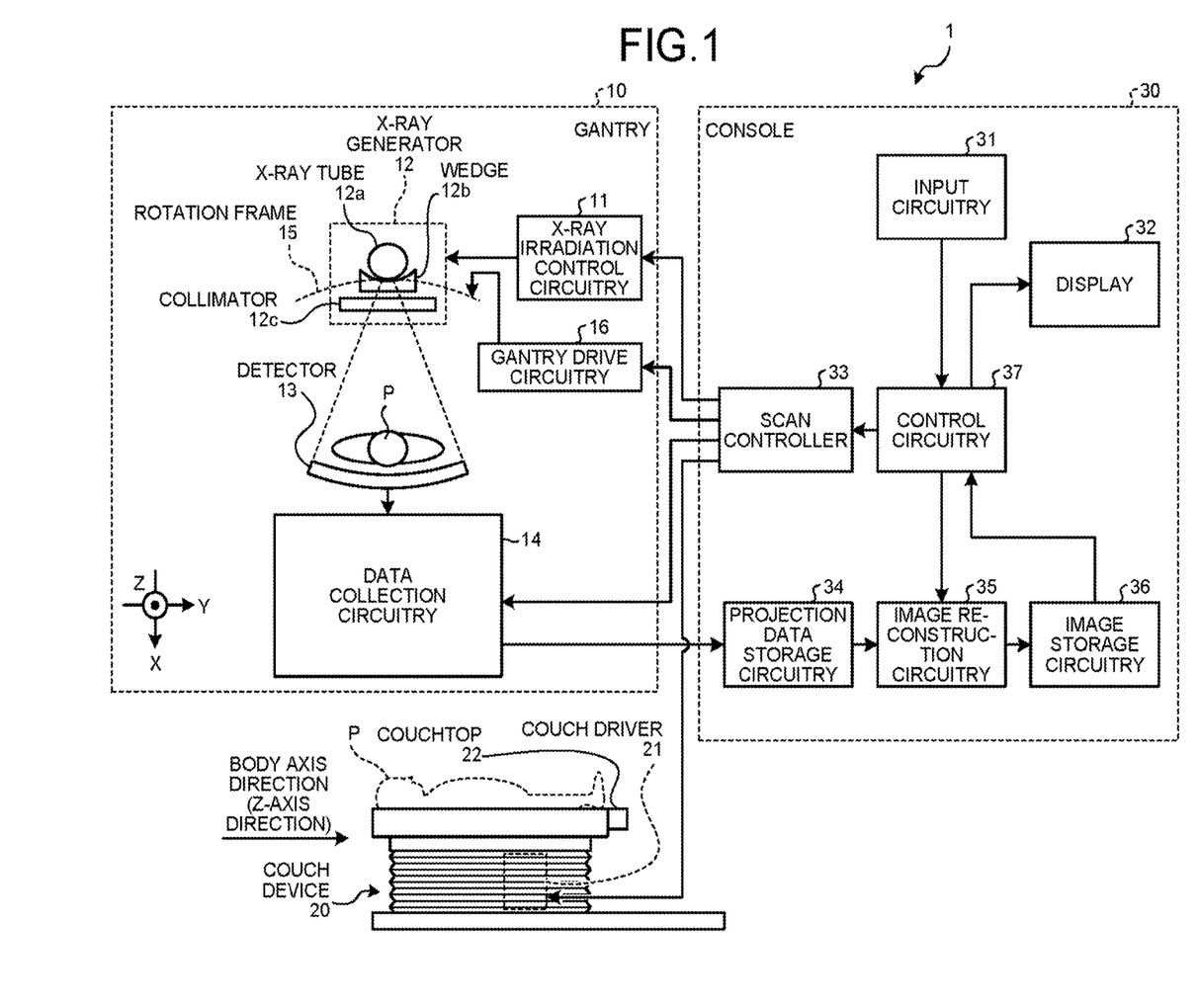
FIG. 1 is a diagram illustrating a configuration example of an X-ray CT apparatus according to a first embodiment.

Described first is a configuration of an X-ray CT apparatus 1 according to a first embodiment. FIG. 1 is a diagram illustrating a configuration example of the X-ray CT apparatus 1 according to the first embodiment. As illustrated in FIG. 1, the X-ray CT apparatus according to the first embodiment includes a gantry 10, a couch device 20, and a console 30.

The gantry 10 emits X-rays to a subject P, detects the X-rays that have passed through the subject P, and outputs the detected X-rays to the console 30. The gantry 10 includes an X-ray irradiation control circuitry 11, an X-ray generator 12, a detector 13, a data collection circuitry 14, a rotation frame 15, and a gantry drive circuitry 16.

The rotation frame 15 is an annular frame that supports the X-ray generator 12 and the detector 13 such that they face each other across the subject P, and is rotated by the gantry drive circuitry 16 to be described later at high-speed in a circular orbit about the subject P.

The X-ray generator 12 generates X-rays and emits the generated X-rays to the subject P. Inc X-ray generator 12 includes an X-ray tube 12a, a wedge 12b, and a collimator 12c.

The X-ray tube 12a is a vacuum tube that emits an X-ray beam to the subject P with application of a high voltage supplied by the X-ray irradiation control circuitry 11 as a high-voltage generator. The X-ray tube 12a emits the X-ray beam to the subject P with the rotation of the rotation frame 15. The X-ray tube 12a generates an X-ray beam with a fan angle and an X-ray beam with a cone angle.

The wedge 12b is an X-ray filter for adjusting the radiation dose of the X-rays emitted from the X-ray tube 12a. Specifically, the wedge 12b is a filter through which the X-rays emitted from the X-ray tube 12a pass to be attenuated so that the X-rays emitted from the X-ray tube 12a to the subject P form a predetermined distribution. For example, the wedge 12b is a filter made of aluminum that gives the X-rays certain target angles and a certain thickness. The wedge is also called, for example, a wedge filter or a bow-tie filter.

The collimator 12c is a slit that narrows down the irradiation range of the X-rays, the radiation dose of which has been adjusted by the wedge 12b under the control of the X-ray irradiation control circuitry 11 to be described later.

The X-ray irradiation control circuitry 11 supplies a high voltage to the X-ray tube 12a as the high-voltage generator. The X-ray tube 12a generates X-rays by using the high voltage supplied from the X-ray irradiation control circuitry 11. The X-ray irradiation control circuitry 11 adjusts the tube voltage and the tube current supplied to the X-ray tube 12a to adjust the radiation dose of the X-rays emitted to the subject P.

The X-ray irradiation control circuitry 11 itches the wedge 12b. The X-ray irradiation control circuitry 11 adjusts the degree of opening of the collimator 12c to adjust the irradiation range (fan angle and cone angle) of the X-rays. In the first embodiment, the operator may manually switch a plurality of wedges.

The gantry drive circuitry 16 rotates the rotation frame 15, so that the X-ray generator 12 and the detector 13 are rotated in the circular orbit about the subject P.

The detector 13 is a two-dimensional array detector (planar detector) that detects the X-rays that have passed though the subject P. The detector 13 includes a plurality of detection elements arrays arranged in the body axis direction of the subject P (in the 2-axis direction in FIG. 1). Each detection elements array is configured by X-ray detection elements for a plurality of channels. Specifically, the detector 13 according to the first embodiment includes X-ray detection elements arranged in a plurality of rows, such as in 320 rows, in the body axis direction of the subject P. The detector 13 can detect, for example, X-rays that have passed through a broad range of the subject P such as a range including the lung and the heart of the subject P.

The data collection circuitry 14 generates projection data by using the X-rays detected by the detector 13, and transmits the generated projection data to a projection data storage circuitry 34 in the console 30.

The couch device 20 is a device on which the subject P is placed, and includes a couch driver 21 and a couchtop as illustrated in FIG. 1. The couch driver 21 moves the couchtop 22 in the Z-axis direction to move the subject P inside the rotation frame 15. The couchtop 22 is a table on which the subject P is placed.

The gantry 10 performs, for example, helical scan in which the gantry 10 scans the subject P helically by rotating the rotation frame 15 while moving the couchtop 22. Alternatively, the gantry 10 performs conventional scan in which, after the couchtop 22 is moved and stopped, the gantry 10 scans the subject P in a fixed position in a circular orbit by rotating the rotation frame 15. In some cases, the gantry 10 performs step-and-shoot scan in which the couchtop 22 is moved at certain intervals and the conventional scan is performed at a plurality of scan areas.

The console 30 receives operations on the X-ray CT apparatus by the operator, and reconstructs X-ray CT image data from the projection data collected by the gantry 10. As illustrated in FIG. 1, the console 30 includes an input circuitry 31, a display 32, a scan controller 33, the projection data storage circuitry 34, an image reconstruction circuitry 35, an image storage circuitry 36, and a control circuitry 37.

The input circuitry 31 includes, for example, a mouse and a keyboard to be used in inputting various instructions and settings from the operator of the X-ray CT apparatus 1, and transfers information of the instructions and the settings received from the operator to the control circuitry 37. For example, the input circuitry 31 receives information such as shoot conditions for X-ray CT image data, reconstruction conditions for reconstructing the X-ray CT image data, and image processing conditions for the X-ray CT image data from the operator.

The display 32 is a monitor to which the operator refers. Under the control of the control circuitry 37, the display 32 displays X-ray CT image data to the operator and displays graphical user interfaces (GUIs) for receiving various instructions and settings from the operator via the input circuitry 31.

The scan controller 33 controls, under the control of the control circuitry 37 to be described later, the operations of the X-ray irradiation control circuitry 11, the gantry drive circuitry 16, the data collection circuitry 14, and the couch driver 21, thereby controlling collection processing of projection data performed by the gantry 10.

The projection data storage circuitry 34 stores therein projection data generated by the data collection circuitry 14. In other words, the projection data storage circuitry 34 stores therein projection data for reconstructing X-ray CT image data.

The image reconstruction circuitry 35 reconstructs X-ray CT image data from the projection data stored in the projection data storage circuitry 34. There are several ways to reconstruct the X-ray CT image data and examples of them include back projection processing. Examples of back projection processing include the filtered back projection (FEE) method and the convolution back projection method. The image reconstruction circuitry 35 performs reconstruction by the successive approximation method. The image reconstruction circuitry 35 performs various types of image processing on the X-ray CT image data to generate image data. The image reconstruction circuitry 35 stores the reconstructed X-ray CT image data and the image data generated by various types of image processing in the image storage circuitry 36. The image storage circuitry 36 stores therein image data generated by the image reconstruction circuitry 35.

The control circuitry 37 controls the operations of the gantry 10, the couch device 20, and the console 30, thereby controlling the entire X-ray CT apparatus 1. Specifically, the control circuitry 37 controls the scan controller 33 to control CT scan performed by the gantry 10. The control circuitry 37 controls the image reconstruction circuitry 35 to control the image reconstruction processing and the image generation processing in the console 30. The control circuitry 37 controls the display 32 to display various types of image data stored in the image storage circuitry 36.

The overall configuration of the X-ray CT apparatus 1 according to the first embodiment has been described. With this configuration, the X-ray CT apparatus 1 according to the first embodiment can prevent an increase in radiation dose and can acquire a high-resolution image of a region that the observer wants to observe. Described here is why conventional X-ray CT apparatus have difficulty in both preventing an increase in radiation dose and acquiring a high-resolution (high-definition) image of a region that the observer wants to observe. In general, to prevent an increase in radiation dose and to acquire a high-resolution image of a region (region of interest) that the observer wants to observe, such a conventional X-ray CT apparatus first scans a large region with low-dose X-rays, and then scans again a region of interest specified from the scanned region to acquire a high resolution image.

To adjust resolution, the X-ray CT apparatus performs signal bundling processing or slice thickness adjustment. In the signal bundling processing, for example, analog signals detected by a plurality of detection elements of the detector are combined in a certain unit in at least one direction of the channel direction and the slice direction. Resolution is adjusted by changing the unit of combination. For example, the X-ray CT apparatus scans in a standard-resolution mode in which four detection elements are combined as one unit, and in a high-resolution mode in which no detection elements are combined. The X-ray CT apparatus scans a large region with low-dose X-rays in the standard-resolution mode. Performing the signal bundling processing in the standard-resolution mode increases the signal-to-noise ratio, whereby the observer can observe the image acquired by the low-dose X-ray scan without any problem.

When a region of interest in the image is specified, the X-ray CT apparatus scans the specified region in the high-resolution mode. In the high-resolution mode in which the signal bundling processing is not performed, the X-ray CT apparatus has a lower signal-to-noise ratio and thus performs a high-dose X-ray scan to increase the signal-to-noise ratio. The number of detection elements combined as one unit in the signal bundling processing is not limited to the above example.

When, for example, resolution is adjusted by adjusting slice thickness, the X-ray CT apparatus performs a scan in the following manner. When, for example, a conventional X-ray CT apparatus collects a high-resolution image, it performs helical scan on a large region with low-dose X-rays in many rows at a high helical pitch, and then performs helical scan again with relatively high-dose X-rays in fewer rows at a low helical pitch on a narrower region that has been set from the scanned image because it needs to be imaged at a high resolution. The X-ray CT apparatus needs a high signal-to-noise ratio to acquire a high-resolution image, which results in an increase in the radiation dose (exposure). The X-ray CT apparatus acquires projection data in this manner, and uses a high-resolution reconstruction algorithm on the projection data to acquire a CT image having a little higher resolution than that of a CT image acquired in an ordinary scan.

Figure 2A:
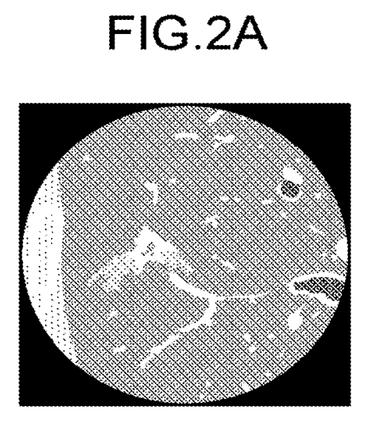
FIGS. 2A and 2B are diagrams illustrating examples of CT images having different resolutions according to the first embodiment.

In other words, the X-ray CT apparatus collects projection data of the whole region of a shooting subject with low-dose X-rays in the standard-resolution mode, in which the signal bundling processing is performed or in which high helical pitch scan is performed. With this processing, a CT image reconstructed from the collected projection data is observed. For example, a standard-resolution CT image illustrated in FIG. 2A is observed.

Figure 2B:
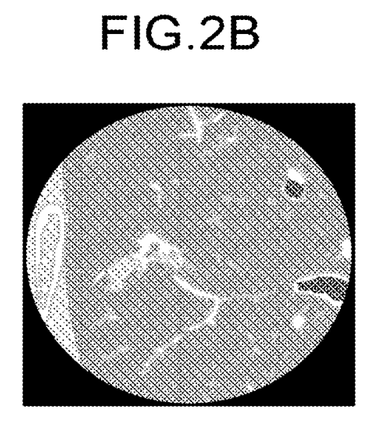

Subsequently, if wanted by the observer, the X-ray CT apparatus reconstructs a high-resolution CT image from projection data collected with high-dose X-rays in the high-resolution mode, in which the signal bundling processing is not performed or in which low helical pitch scan is performed. With this processing, the high-resolution CT image is observed by the observer. In other words, a high-resolution CT image illustrated in FIG. 23 is observed. FIGS. 2A and 2B are diagrams illustrating examples of CT images having different resolutions according to the first embodiment.

When the X-ray CT apparatus performs reconstruction by back projection of the projection data, it needs projection data of a rather large region including the region of interest. If not, artifact may occur and the X-ray CT apparatus fails to acquire a high-resolution CT image that is easy to observe. Thus, when the conventional X-ray CT apparatus collects projection data in the high-resolution mode, it emits high-dose X-rays to a broad range of a subject, resulting in an increase in the radiation dose. The X-ray CT apparatus 1 according to the first embodiment, on the other hand, can prevent an increase in radiation dose and can acquire a high-resolution image of a region that the observer wants to observe under the control of the control circuitry 37 to be described below in detail.

Figure 3:
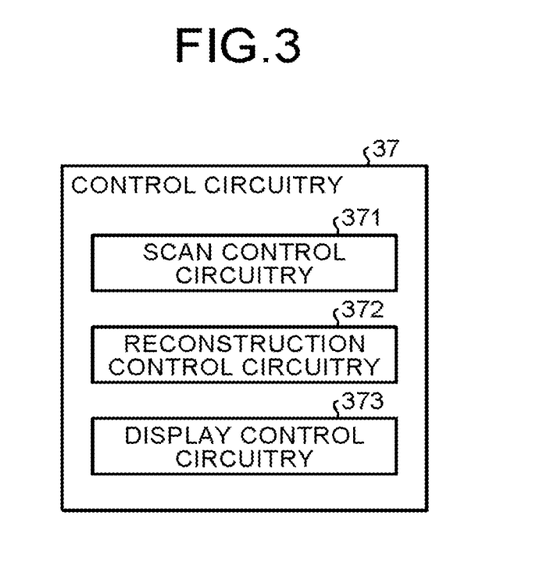
FIG. 3 is a diagram illustrating an example of a configuration of a control circuitry according to the first embodiment.

FIG. 3 is a diagram illustrating an example of a configuration of the control circuitry 37 according to the first embodiment. As illustrated in FIG. 3, the control circuitry 37 includes, for example, a scan control circuitry 371, a reconstruction control circuitry 372, and a display control circuitry 373. The scan control circuitry 371 collects first projection data of a first X-ray irradiation range. The scan control circuitry 371 collects second projection data of a second X-ray irradiation region included in the first X-ray irradiation region in a higher resolution than that of the first projection data.

Figure 4:
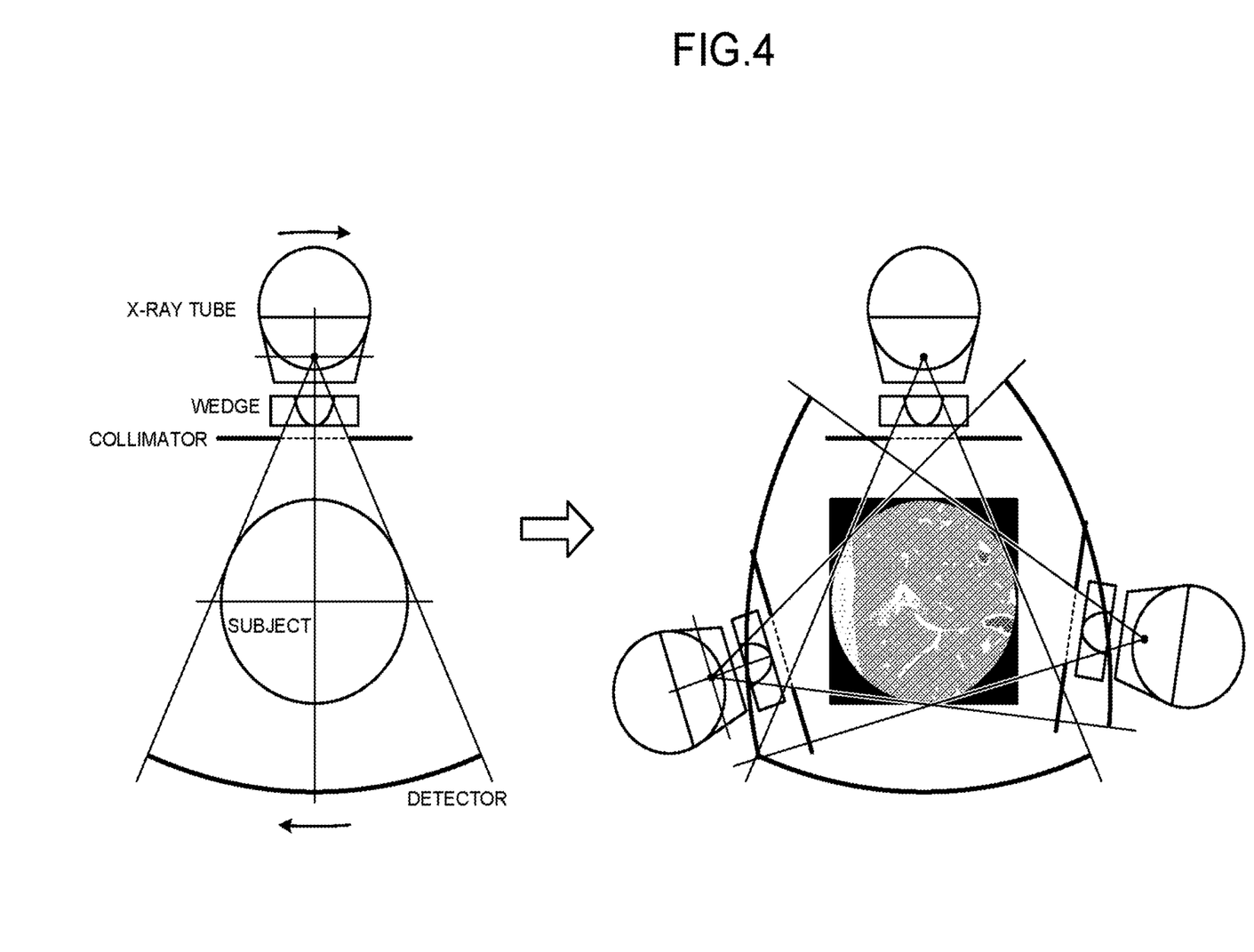
FIG. 4 is a diagram illustrating an example of scan control in a standard-resolution mode performed by a scan control circuitry according to the first embodiment.

Specifically, the scan control circuitry 371 causes a low-dose scan in the standard-resolution mode on a whole subject part (with respect to a whole cross section at a part of the subject in the slice direction). The scan control circuitry 371 controls the collimator 12C to fully open in the channel direction. FIG. 4 is a diagram illustrating an example of scan control in the standard-resolution mode performed by the scan control circuitry 371 according to the first embodiment.

As illustrated in FIG. 4, for example, the scan control circuitry 371 controls the collimator 12C to open so that the whole cross section is included in the irradiation region of the X-rays until the X-ray tube 12A completes one revolution about the subject. In other words, the scan control circuitry 371 causes collection processing for collecting projection data in the standard-resolution mode without narrowing down the collimator 12C in the channel direction. Although not illustrated in FIG. 4, the scan control circuitry 371 controls the collimator 12C to narrow down in the slice direction as appropriate.

The X-ray CT apparatus 1 may perform the above-described low-dose X-ray scan in standard resolution in any manner as long as it can acquire a CT image that is clear enough to specify the region of interest in the image. In other words, the scan control circuitry 371 may perform a scan in the standard-resolution mode with lower-dose X-rays, where the signal bundling processing described above is performed to increase the signal-to-noise ratio. Alternatively, the scan control circuitry 371 may perform a low-dose scan without performing the signal bundling processing. In the latter case, the scan control circuitry 371 scans a subject with low radiation dose and no signal bundling processing, which results in a lower signal-to-noise ratio, and thus, a noisy CT image. To reduce noise, the scan control circuitry 371 performs, after performing a low-dose scan with no signal bundling processing, smoothing filter processing on the acquired noisy image to generate an easy-to-observe image. The smoothing filter processing may be performed on the data before reconstruction or on the data after the reconstruction. Alternatively, the smoothing filter processing may be performed on the data both before and after the reconstruction.

In some cases, a CT image includes an electrical noise caused by an analog signal processing circuit. The level of such an electrical noise may be higher than that of a random noise that occurs on the whole image. Performing the signal bundling processing, in which a plurality of signals are processed in one circuit, to acquire a standard-resolution CT image can prevent such an electrical noise from occurring. Thus, performing the signal bundling processing, which can prevent noise from occurring and increase the signal-to-noise ratio, can contribute to further reduction in radiation dose. In other words, as long as the reduction in radiation dose is concerned, it is desirable to acquire a standard-resolution CT image by performing the signal bundling processing.

The scan control circuitry 371 controls collection processing for collecting a high-resolution CT image of a region of interest specified in the standard-resolution CT image. The scan control circuitry 371 also controls the collimator in performing the high-resolution mode scan. The details of the control by the scan control circuitry 371 in the high-resolution mode scan will be described later.

Referring back to FIG. 3, the reconstruction control circuitry 372 controls the image reconstruction circuitry 35 to reconstruct a CT image by the convolution back projection method from the projection data collected by the scan control circuitry 371 in the standard-resolution mode. The reconstruction control circuitry 372 then controls the image reconstruction circuitry 35 to perform reconstruction by the successive approximation method by using high-resolution projection data on the reconstructed standard-resolution CT image as an initial image. How the reconstruction control circuitry 372 performs reconstruction by the successive approximation method will be described later.

Figure 5:
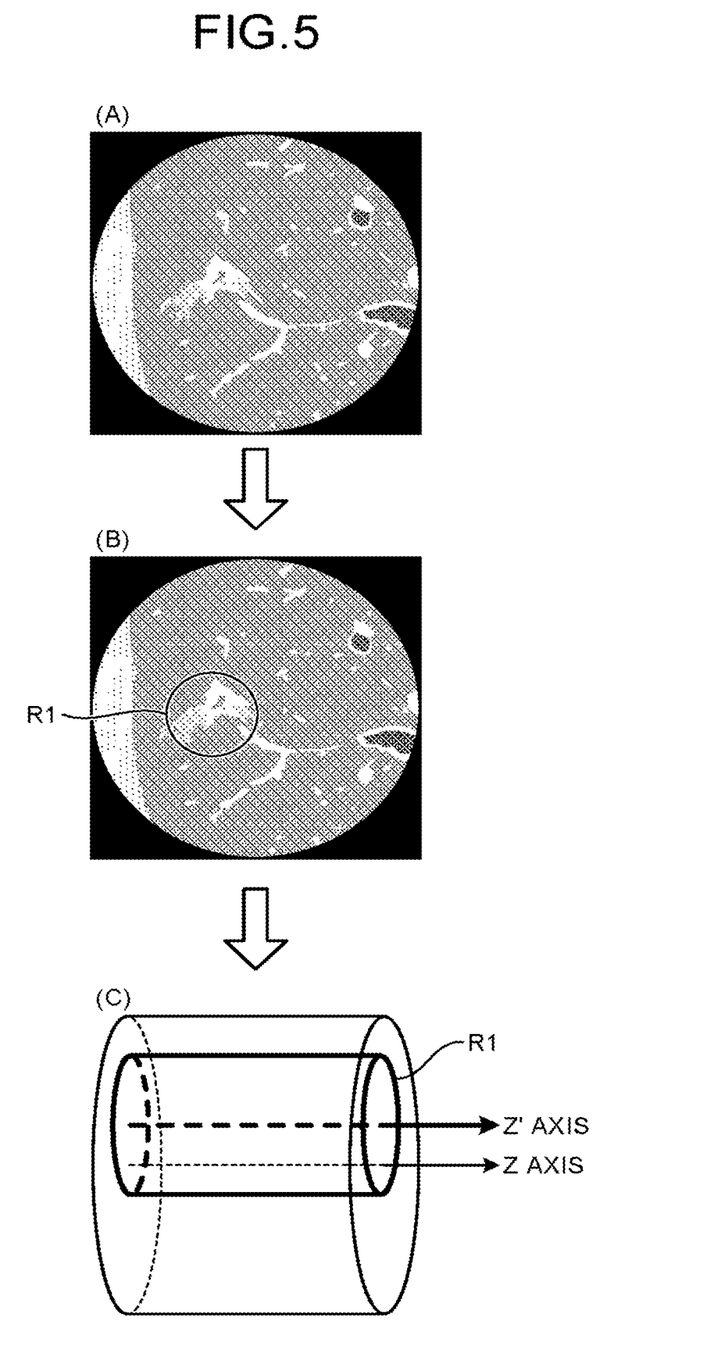
FIG. 5 is a diagram illustrating an example of processing performed by an input circuitry according to the first embodiment.

The display control circuitry 373 controls the display 32 to display the CT image generated under the control of the reconstruction control circuitry 372. For example, the display control circuitry 373 causes the display 32 to display a standard-resolution CT image. The observer refers to the CT image displayed on the display 32 and selects, via the input circuitry 31, a region of interest that the observer wants to observe in high resolution. In other words, the input circuitry 31 receives a specifying operation for specifying, from a region of a first medical image acquired such that it contains less noise, a region for which a second medical image that is a higher-resolution higher-definition) image than a first medical image is acquired. For example, the input circuitry 31 receives a specifying operation for specifying the second X-ray irradiation region. FIG. 5 is a diagram illustrating an example of processing performed by the input circuitry 31 according to the first embodiment. FIG. 5(A) illustrates a standard-resolution CT image displayed on the display 32. FIG. 5(B) illustrates a CT image in which a region of interest is specified by the operator. FIG. 5(C) illustrates an example of a specified region of the region of interest.

The display control circuitry 373, for example, causes the display 32 to display a standard-resolution CT image as illustrated in FIG. 5(A), and the input circuitry 31 receives a specifying operation on a region R1 of interest from an observer as illustrated in FIG. 5(F). The scan control circuitry 371 specifies, in the projection data, the position of the region R1 of interest that has been specified via the input circuitry 31. In other words, as illustrated in FIG. 5(C), the scan control circuitry 371 specifies a three-dimensional region for the region R1 of interest in the scanned projection data, with the Z' axis that is parallel the Z axis, which is the central axis of the scanned projection data in the slice direction, being the central axis of the three-dimensional region.

For example, the scan control circuitry 171 specifies a three-dimensional region for the region R1 on the basis of coordinate information of the projection data or the like. Although, with reference to FIG. 5, described is a case in which the region R1 of interest is specified in a two-dimensional CT image, the embodiments are not limited to this. The region R1 of interest may be specified in a three-dimensional CT image. In this case, for example, the region R1 of interest may be specified in the three-dimensional CT image displayed as illustrated in FIG. 5(C).

The size of e region R1 of interest can be determined by the observer to any sire. Although, in FIG. 5, the region R1 of interest is specified in the form of a circle (circular cylinder), the embodiments are not limited to this. The region R1 of interest may be specified in the form of a quadrilateral (quadrangular prism).

Figure 6:
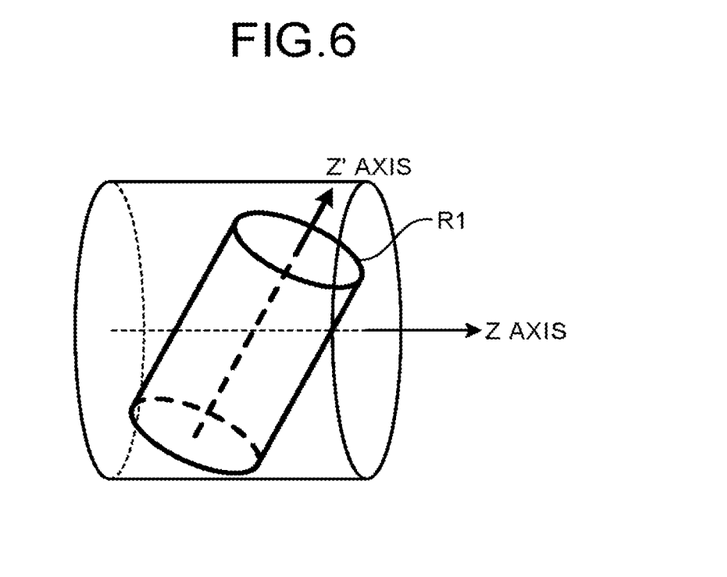
FIG. 6 is a diagram illustrating an example of a region of interest specified by the scan control circuitry according to the first embodiment.

In addition to specifying a region with the Z' axis being parallel to the Z axis, the scan control circuitry 371 can also specify the position of the region R1 of interest that is set such that the Z' axis has a certain inclination angle to the Z axis. In other words, the input circuitry 31 receives a specifying operation for specifying, as a certain region, a region with an axis parallel to the slice direction of the three-dimensional image data, or a region with an axis having a certain inclination angle to the slice direction of the three-dimensional image data. FIG. 6 is a diagram illustrating an example of a region of interest specified by the scan control circuitry 371 according to the first embodiment.

As illustrated in FIG. 6, for example, the scan control circuitry 371 specifies, in the projection data, the position of the region R1 of interest that has a certain inclination angle to the Z axis of the projection data. In this case, for example, the display control circuitry 373 causes the display 32 to display a three-dimensional CT image as illustrated in FIG. 6. As illustrated in FIG. 6, the input circuitry 31 receives a specifying operation for specifying the region R1 of interest with the Z' axis having a certain inclination angle to the axis being the reference axis.

Alternatively, the display control circuitry 373 causes the display 32 to display multi-planar reconstruction (MPR) images of the three orthogonal sections, and the input circuitry 31 receives a setting of an oblique section. With this processing, the region R1 of interest is selected, and the scan control circuitry 371 specifies, in the projection data, the position of the region R1 of interest having a certain inclination angle to the Z axis of the projection data as illustrated in FIG. 6.

As described above, the scan control circuitry 371 specifies, in projection data, the position of the region R1 of interest having a certain inclination angle to the Z axis of the projection data. In the same manner as described above, the scan control circuitry 371 specifies a three-dimensional region of the region R1 of interest on the basis of information such as coordinate information of the projection data. The scan control circuitry 371 calculates, from the coordinate information of the projection data, information on the region R1 of interest such as the size of the cross section perpendicular to the Z axis, the matrix size, the length in the Z' axis direction, and the positional relation (orientation and distance, for example) between the Z' axis and the Z axis, and keeps the calculated information as information for specifying the regions.

Figure 7:
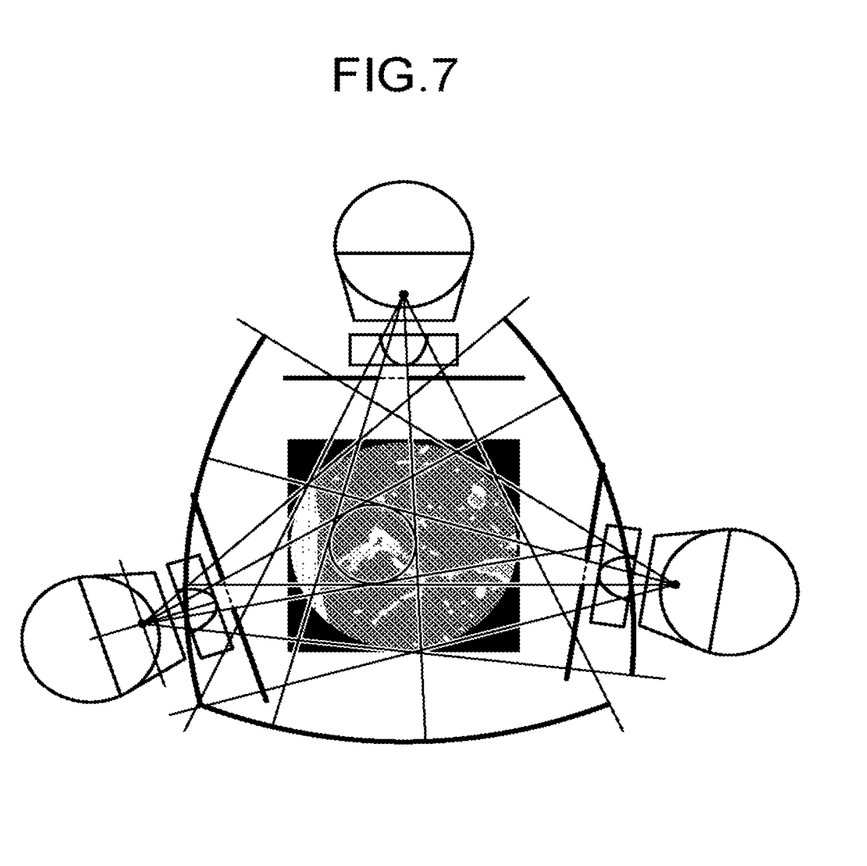
FIG. 7 is a diagram illustrating an example of scan control in a high-resolution mode performed by the scan control circuitry according to the first embodiment.

As described above, when the region R1 of interest is specified in the standard-resolution CT image, the scan control circuitry 371 adjusts the irradiation region of X-rays in the slice direction and the channel direction so that the specified region R1 of interest is irradiated with the X-rays. FIG. 7 is a diagram illustrating an example of scan control in the high-resolution mode performed by the scan control circuitry 371 according to the first embodiment. As illustrated in FIG. 7, for example, the scan control circuitry 371 sets an open position condition of the collimator for each rotation angle of the scanner.

The scan control circuitry 371 sets the per position condition of the collimator for each rotation angle of the scanner such that the scanner scans a region including a certain margin for expected movements of the subject's body. The scan control circuitry 371 collects projection data of the region R1 of interest by scanning in the high-resolution mode while the scan control circuitry 371 keeps changing the open position of the collimator at each rotation angle of the scanner in accordance with the set condition. For example, the can control circuitry 371 collects projection data of the region R1 of interest with high-dose X-rays in the high-resolution mode, in which the signal bundling processing is not performed.

To reduce radiation dose, it is desirable to dynamically control the open position of the collimator at each rotation angle of the scanner. In a practical operation, however, moving the open position of the collimator during the scan may be difficult in some cases depending on conditions such as scan speed or control speed. In such cases, the blades of the collimator may be fixed to a maximum open position for one revolution of the X-ray tube. In this case, the total radiation dose can be reduced compared to standard-resolution scan, in which the collimator is fully open during the scan. FIG. 7 illustrate a case in which the region of interest is assumed as a two-dimensional region. When the region of interest is set as a three-dimensional region, the scan control circuitry 371 causes a collimator (slit) that controls the beam thickness (slice thickness) to operate in the same manner.

When the region of interest is scanned in the high-resolution mode as illustrated in FIG. 7, the reconstruction control circuitry 372 causes reconstruction processing by the successive approximation method by using the projection data collected in the high-resolution mode on a standard-resolution CT image reconstructed by the convolution back projection method as an initial image. In other words, the reconstruction control circuitry 372 updates the image such that the pixels of the region of interest in the standard-resolution CT image are updated by using the projection data of the region of interest.

Figure 8:
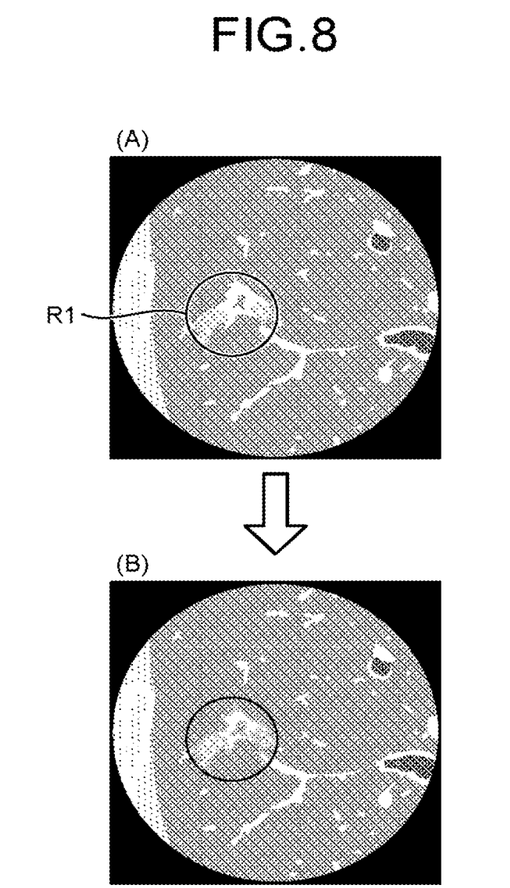
FIG. 8 is a diagram schematically illustrating processing performed by a reconstruction control circuitry according to the first embodiment.

FIG. 8 is a diagram schematically illustrating processing performed by the reconstruction control circuitry 372 according to the first embodiment. When, for example, the region R1 of interest is specified in a standard-resolution CT image as illustrated in FIG. A), the reconstruction control circuitry 372 updates the region R1 of interest with a high-resolution CT image as illustrated in FIG. 8(B). For example, the display control circuitry 373 may control the display 32 to display the CT image illustrated in FIG. 8(B).

Figure 9:
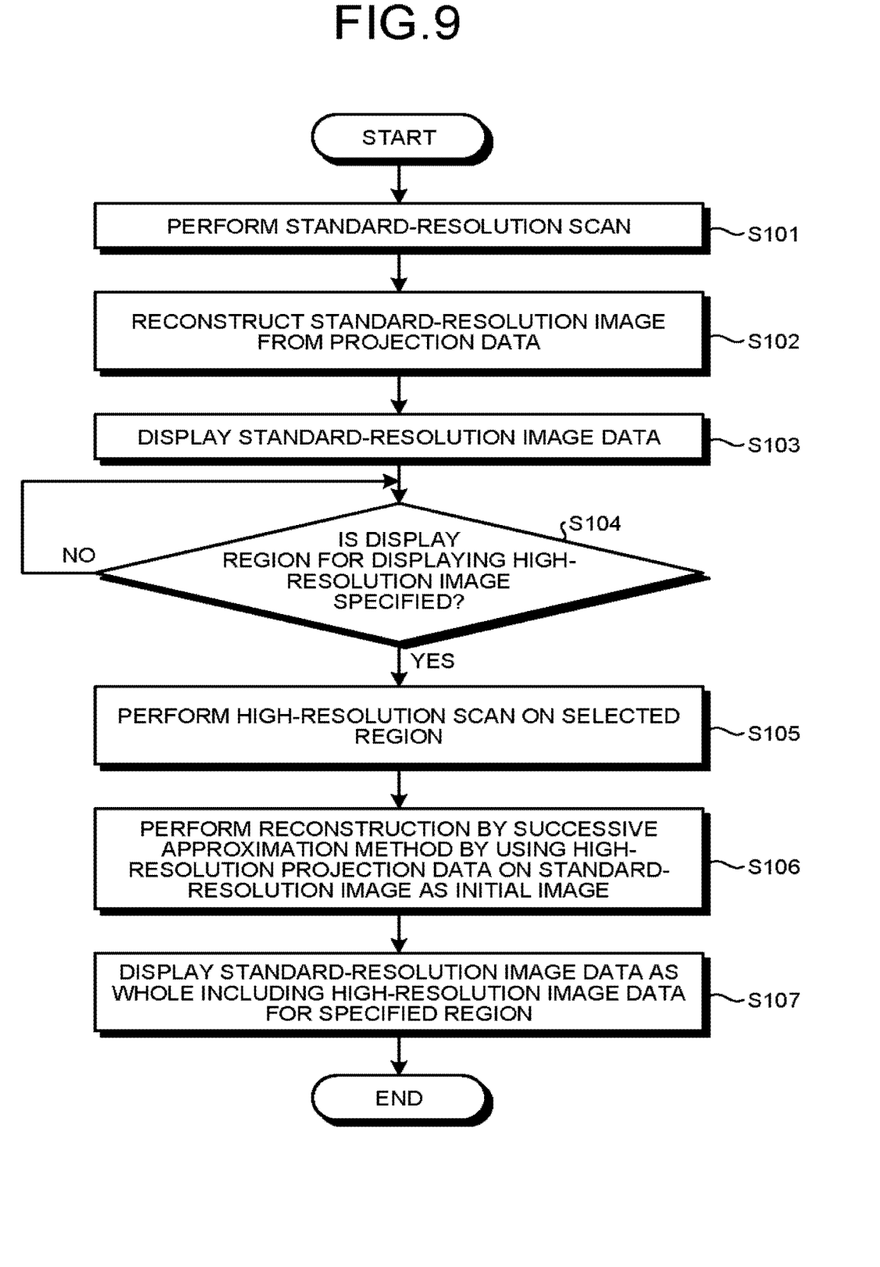
FIG. 9 is a flowchart illustrating an example of processing performed by the X-ray CT apparatus according to the first embodiment.

Described next is processing performed by the X-ray CT apparatus according to the first embodiment with reference to FIG. 9. FIG. 9 is a flowchart illustrating an example of processing performed by the X-ray CT apparatus 1 according to the first embodiment.

As illustrated in FIG. 9, for example, the X-ray CT apparatus 1 according to the first embodiment performs a standard-resolution scan (Step S101), and reconstructs standard-resolution image data from projection data (Step S102). The display control circuitry 373 causes the display 32 to display the reconstructed standard-resolution image data (Step 3103).

The input circuitry 31 determines whether a display region (the region R1 of interest, for example) in which a high-resolution image will be displayed has been specified (Step S104). If the input circuitry 31 determines that the display region has been specified (Yes at Step S104), the scan control circuitry 371 causes a high-resolution scan on the selected region (Step S105).

The reconstruction control circuitry 372 performs reconstruction by the successive approximation method by using the high-resolution projection data on the standard-resolution image as an initial image (Step S106). The display control circuitry 373 causes the display 32 to display image data that is standard-resolution image data as a whole but includes high-resolution image data in a specified region (Step S107).

According to the first embodiment described above, the scan control circuitry 371 collects standard-resolution projection data of a whole cross section and collects high-resolution projection data of a region of interest included in the whole cross section. The reconstruction control circuitry 372 performs reconstruction by the successive approximation method by using the high-resolution projection data of the region of interest on a CT image reconstructed from the standard-resolution projection data collected by the scan control circuitry 371 as an initial image. Thus, the X-ray CT apparatus 1 according to the first embodiment can adjust a region, for which high-resolution image data is acquired, to a maximum possible limit of the region of interest. With this configuration, the X-ray CT apparatus 1 can prevent an increase in radiation dose and can acquire a high-resolution image of a region that the observer wants to observe.

According to the first embodiment, the input circuitry 31 receives a specifying operation for specifying the second X-ray irradiation region. The scan control circuitry 371 adjusts the X-ray irradiation region in the slice direction and the channel direction so that the region of interest, on which the specifying operation is received by the input circuitry 31, is irradiated with X-rays. Thus, the X-ray CT apparatus 1 according to the first embodiment can easily control the irradiation of X-rays, can prevent an increase in radiation dose, and can easily acquire a high-resolution image of a region that the observer wants to observe.

According to the first embodiment, the scan control circuitry 371 continues adjusting the irradiation region such that the region of interest is kept irradiated with X-rays while the X-rays are being emitted. Thus, the X-ray CT apparatus 1 according to the first embodiment can reduce radiation dose as much as possible.

According to the first embodiment, the reconstruction control circuitry 372 reconstructs a CT image from standard-resolution projection data by the convolution back projection method, and performs reconstruction by the successive approximation method by using high-resolution projection data on the standard-resolution CT image as an initial image. Thus, the X-ray CT apparatus 1 according to the first embodiment can be easily implemented.

According to the first embodiment, the display control circuitry 373 controls a display to display a medical image configured by a CT image reconstructed by the reconstruction control circuitry 372, the CT image in which a position corresponding to the region of interest is imaged in a higher resolution than that of the entire CT image. Thus, the X-ray CT apparatus 1 according to the first embodiment facilitates the observation by the observer.

Second Embodiment

Although the first embodiment has been described so far, the present disclosure may be implemented in various other forms than the first embodiment described above.

Although, in the first embodiment, the medical image diagnosis apparatus is described in the context of an X-ray CT apparatus, the embodiments are not limited to this. For example, the medical image diagnosis apparatus may be an X-ray diagnosis apparatus.

The constituent elements of the apparatus illustrated in the drawings of the first embodiment above are of a functional and conceptual nature, and are not necessarily physically configured as illustrated in the drawings of the first embodiment. In other words, specific forms of separation and integration of the apparatus are not limited to those illustrated in the drawings, and all or some parts thereof can be functionally or physically separated or integrated in any circuitry depending on, for example, various loads and usage. Furthermore, all or some of the processing functions of the apparatus may be implemented by a central processing unit (CPU) and a computer program analyzed and executed by the CPU, or may be implemented as hardware using a wired logic.

The control method described in the first embodiment can be performed by executing a control program prepared in advance on a computer such as a personal computer or a workstation. This control program can be distributed via a network such as the Internet. The control program can be recorded in a computer-readable recording medium such as a hard disk, a flexible disk (FD), a compact disc read only memory (CD-ROM), a magneto-optical (MO), or a digital versatile disc (DVD), and can be executed by the computer by reading the control program from the recording medium.

As described above, according to the first and the second embodiments, an increase in radiation dose can be prevented and a high-resolution image of a region that an observer wants to observe can be acquired.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claim, and their equivalents are intended to cover such forms or modifications as would fall within the scope and spirit of the inventions.

What is claimed is:

1. A medical image diagnosis apparatus, comprising:
processing circuitry configured to:
    perform a first scan to acquire first projection data by a helical scan;
    receive a specifying operation for specifying, on a first medical image based on the first projection data, a region for which a second medical image that is a higher-resolution image than the first medical image is acquired;
    adjust an irradiation region of X-rays in a slice direction and in a channel direction so that a part corresponding to the region on which the specifying operation is received is irradiated with the X-rays;
    perform a second scan to acquire second projection data for the irradiation region by a conventional scan, or a helical scan with narrower pitch than the helical scan that acquired the first projection data; and
    generate the second medical image by performing a successive approximation reconstruction of the second projection data using the first medical image including a region corresponding to a region of the second scan as an initial image for the successive approximation reconstruction.

2. The medical image diagnosis apparatus according to claim 1, wherein the processing circuitry is further configured to continue adjusting the irradiation region such that the region on which the specifying operation is received is kept irradiated with the X-rays while the X-rays are being emitted.

3. The medical image diagnosis apparatus according to claim 1, wherein the processing circuitry is further configured to reconstruct the first medical image based on the first projection data by a convolution back projection method.

4. The medical image diagnosis apparatus according to claim 1, wherein the processing circuitry is further configured to generate a medical image configured by the first medical image reconstructed, the first medical image in which a position corresponding to the region on which the specifying operation is received is imaged by the second medical image that is a higher-resolution image than the first medical image.

5. The medical image diagnosis apparatus according to claim 4, wherein the processing circuitry is further configured to control a display to display the medical image.

6. The medical image diagnosis apparatus according to claim 1, wherein the processing circuitry is further configured to perform the first scan such that a noise contained in the first medical image is reduced.

7. A control method, comprising:
performing a first scan to acquire first projection data by a helical scan;
receiving a specifying operation for specifying, on a first medical image based on the first projection data, a region for which a second medical image that is a higher-resolution image than the first medical image is acquired;
adjusting an irradiation region of X-rays in a slice direction and a channel direction so that a part corresponding to the region on which the specifying operation is received is irradiated with the X-rays;
performing a second scan to acquire second projection data for the irradiation region by a conventional scan, or a helical scan with narrower pitch than the helical scan that acquired the first projection data; and
generating the second medical image by performing a successive approximation reconstruction of the second projection data using the first medical image including a region corresponding to a region of the second scan as an initial image for the successive approximation reconstruction.

* * * * *